United States Patent
Chmielewski et al.

(10) Patent No.: US 10,092,674 B2
(45) Date of Patent: Oct. 9, 2018

(54) ABSORBENT STRUCTURE WITH DRYNESS LAYER

(71) Applicant: EAM Corporation, Jesup, GA (US)

(72) Inventors: Harry J. Chmielewski, Raleigh, NC (US); Paul Ducker, Brunswick, GA (US)

(73) Assignee: ATTENDS HEALTHCARE PRODUCTS, INC., Greenville, NC (US)

(*) Notice: Subject to any disclaimer, the term of this patent is extended or adjusted under 35 U.S.C. 154(b) by 611 days.

(21) Appl. No.: 14/212,969

(22) Filed: Mar. 14, 2014

(65) Prior Publication Data

US 2014/0276510 A1   Sep. 18, 2014

Related U.S. Application Data

(60) Provisional application No. 61/789,444, filed on Mar. 15, 2013.

(51) Int. Cl.
*A61F 13/15* (2006.01)
*A61F 13/20* (2006.01)
(Continued)

(52) U.S. Cl.
CPC ............ *A61L 15/58* (2013.01); *A61F 13/531* (2013.01); *A61F 13/539* (2013.01); *A61L 15/28* (2013.01); *A61L 15/40* (2013.01); *A61F 13/5323* (2013.01); *A61F 2013/530116* (2013.01); *A61F 2013/530489* (2013.01); *A61F 2013/530496* (2013.01)

(58) Field of Classification Search
CPC .......... A61L 15/28; A61L 15/40; A61L 15/58; C08L 1/02; A61F 13/531; A61F 13/5323; A61F 13/539; A61F 2013/530489; A61F 2013/530496
See application file for complete search history.

(56) References Cited

U.S. PATENT DOCUMENTS

| 4,573,986 A | 3/1986 | Minetola et al. |
| 5,486,167 A | 1/1996 | Dragoo et al. |

(Continued)

FOREIGN PATENT DOCUMENTS

| WO | 1996005790 | 2/1996 |
| WO | 2014144131 | 9/2014 |

OTHER PUBLICATIONS

Ducker, Paul M.; Corrected Notice of Allowability for U.S. Appl. No. 14/212,754, filed Mar. 14, 2014, dated Sep. 25, 2015, 8 pgs.
(Continued)

*Primary Examiner* — Michelle M Kidwell (57) ABSTRACT

An absorbent structure including a dryness layer laminate is disclosed, with the structure suitable for use in disposable absorbent products such as for infant or incontinence care. The dryness layer laminate is positioned adjacent an associated absorbent core, between the absorbent core and the wearer, for enhancing surface dryness and comfort for the wearer. The dryness layer laminate comprises adhesive fibers or filaments, and particulate superabsorbent, and is configured to permit liquid to pass through the laminate to the associated absorbent core, while acting to remove liquid from the surface of the absorbent structure positioned adjacent to the wearer.

20 Claims, 2 Drawing Sheets

(51) Int. Cl.
*A61L 15/58* (2006.01)
*A61F 13/539* (2006.01)
*A61L 15/28* (2006.01)
*A61L 15/40* (2006.01)
*A61F 13/531* (2006.01)
*A61F 13/532* (2006.01)
*A61F 13/53* (2006.01)

(56) References Cited

U.S. PATENT DOCUMENTS

| | | | | |
|---|---|---|---|---|
| 5,520,673 | A * | 5/1996 | Yarbrough | A61F 13/512 604/358 |
| 5,558,655 | A * | 9/1996 | Jezzi | A61F 13/534 604/368 |
| 5,593,399 | A | 1/1997 | Tanzer et al. | |
| 5,944,706 | A * | 8/1999 | Palumbo | A61F 13/539 604/368 |
| 6,037,518 | A | 3/2000 | Guidotti et al. | |
| 6,191,340 | B1 | 2/2001 | Carlucci et al. | |
| 6,316,687 | B1 * | 11/2001 | Davis | A61F 13/15203 604/372 |
| 6,372,953 | B1 | 4/2002 | Young et al. | |
| 6,380,456 | B1 | 4/2002 | Goldman | |
| 6,436,234 | B1 * | 8/2002 | Chen | A61F 13/15203 162/109 |
| 6,455,114 | B1 | 9/2002 | Goldhirsch et al. | |
| 6,479,415 | B1 * | 11/2002 | Erspamer | A61F 13/534 442/381 |
| 6,610,903 | B1 | 8/2003 | Latimer et al. | |
| 6,667,424 | B1 * | 12/2003 | Hamilton | A61F 13/15 604/360 |
| 6,746,976 | B1 | 6/2004 | Urankar et al. | |
| 6,923,926 | B2 * | 8/2005 | Walter | A61F 13/1565 156/200 |
| 7,910,797 | B2 * | 3/2011 | Nandrea | A61F 13/42 128/886 |
| 8,039,684 | B2 | 10/2011 | Guidotti et al. | |
| 9,238,089 | B2 | 1/2016 | Chmielewski et al. | |
| 2003/0225384 | A1 * | 12/2003 | Zenker | A61F 13/535 604/367 |
| 2010/0256584 | A1 * | 10/2010 | Litvay | A61F 13/53 604/372 |
| 2011/0162989 | A1 * | 7/2011 | Ducker | A61F 13/5323 206/389 |
| 2012/0004632 | A1 | 1/2012 | Zhang et al. | |

OTHER PUBLICATIONS

Ducker, Paul M.; Issue Notification for U.S. Appl. No. 14/212,754, filed Mar. 14, 2014, dated Dec. 29, 2015, 1 pg.
Ducker, Paul M.; Non-Final Office Action for U.S. Appl. No. 14/212,754, filed Mar. 14, 2014, dated Jan. 14, 2015, 21 pgs.
Ducker, Paul M.; Notice of Allowance for U.S. Appl. No. 14/212,754, filed Mar. 14, 2014, dated Aug. 17, 2015, 9 pgs.
Ducker, Paul M.; U.S. Patent Application entitled: Absorbent Structure With Discrete Acquisition Cells, having U.S. Appl. No. 14/212,754, filed Mar. 14, 2014, 30 pgs.
Ducker, Paul M.; International Preliminary Report for PCT Application No. PCT/US2014/028292, filed Mar. 14, 2014, dated Sep. 15, 2015, 6 pgs.
Ducker, Paul M.; International Search Report and Written Opinion for PCT Application No. PCT/US2014/028292, filed Mar. 14, 2014, dated Aug. 11, 2014, 7 pgs.
Chmielewski, Harry J.; International Preliminary Report on Patentability for PCT Application No. PCT/US2014/028414, filed Sep. 15, 2015, 9 pgs.
Chmielewski, Harry J.; International Search Report and Written Opinion for PCT Application No. PCT/US2014/028414, filed Mar. 14, 2014, 10 pgs.
Ducker, Paul; U.S. Provisional Application entitled: Absorbent Structures, having U.S. Appl. No. 61/789,444, filed Mar. 15, 2013, 33 pgs.
International Search Report and Written Opinion for corresponding PCT application No. PCT/US2014/028414.

\* cited by examiner

FIG_1

FIG_2

ABSORBENT STRUCTURE WITH DRYNESS LAYER

FIELD OF THE INVENTION

The present invention relates generally to disposable absorbent products such as infant diapers, adult incontinence briefs, pull-up underwear and bladder control pads, and more particularly to an absorbent structure including a dryness layer laminate positioned to enhance surface dryness for the comfort of the wearer.

BACKGROUND OF THE INVENTION

Disposable absorbent products have met with widespread acceptance in the marketplace for a variety of applications, including infant and adult incontinence care, in view of the manner in which such products can provide effective and convenient liquid absorption and retention while maintaining the comfort of the wearer. However, experience has shown that a need exists for thinner, more discreet, garment-like products that can exhibit a dry surface to the skin during use. Small quantities of liquid trapped in nonwoven fabric layers on the surface of an absorbent product can undesirably hydrate the stratum corneum, the barrier layer of the skin, and increase the rate of diffusion of skin irritants into the skin. Potential skin irritants are present in urine and feces, as well as in skin cleaning products.

In the design of conventional wood pulp fluff/superabsorbent polymer (SAP) absorbent cores, it is widely recognized that cores with higher concentrations of superabsorbent polymer exhibit longer (i.e. poorer) acquisition times and lower (i.e. better) liquid rewet. Furthermore, it follows that a z-direction gradient of superabsorbent polymer, with a SAP-rich surface concentration, will also exhibit longer (i.e. poorer) acquisition times and lower (i.e. better) rewet relative to a core with a homogeneous distribution of SAP. It has been difficult, however, to find ways to boost the dryness of an absorbent core without generating unacceptably long acquisition times. Long acquisition times are unwanted because they promote leakage from an absorbent product.

Conventional technology to improve the acquisition time of cores with increasingly high concentrations of SAP has involved the use of nonwoven surface layers that promote liquid spreading over the surface of a slowly absorbing core in order to allow absorption to occur over a greater surface area. This surface spreading of free liquid often leads to leakage from the side of the core, and/or leakage at the front of the core.

SUMMARY OF THE INVENTION

This present invention is directed to an adhesively-bonded laminate of superabsorbent polymer, or dryness layer, that can be placed on the surface of an absorbent core to enhance surface dryness without a meaningful increase in liquid acquisition time. The invention is the result of the unexpected observation that there is an optimal range of basis weight of superabsorbent polymer in the laminate that is high enough to provide a meaningful boost in surface dryness and yet low enough to provide the required liquid permeability for good liquid acquisition. Related to the optimal basis weight of superabsorbent polymer in the laminate is a relatively high variability of distribution of superabsorbent polymer in the laminate to permit liquid to pass more freely through it. It is preferred to have regions in the laminate of rarified distribution of individual SAP particles. The variability in distribution of superabsorbent polymer in the laminate is associated with a domain size of the order of 700 mm$^2$, about the area of a circle with a diameter of 30 mm. This important feature helps to explain unexpected results of the present invention; i.e. as to why the superabsorbent polymer does not block liquid transport into the core as normally might be expected. Variability in the superabsorbent polymer basis weight of the present invention may help liquid to pass through the laminate while sufficient superabsorbent polymer in the laminate slowly absorbs liquid trapped in the nonwoven surface layers of an absorbent product, keeping the surface next to the wearer unexpectedly dry.

The dryness layer has been shown to improve the surface dryness of an absorbent core on two hierarchical levels: the first is measured by Rewet which is a measure of liquid that can be expressed from a hydrated core under pressure. Six or more grams of liquid can be expressed from a wet core, whereas when less than one gram of liquid can be expressed from the core, it will have a surface that is dry to the touch. The second measure of dryness, called Plate Wetness, to be fully discussed in later sections, is related to smaller quantities of liquid that can be trapped in the nonwoven surface layers of an absorbent product, or between a nonwoven surface layer and the skin. This liquid can be present at levels of several tenths of a gram of liquid, and values less than 0.1 gram have been achieved with the use of a dryness layer described here. Notably, disposition of the dryness layer laminate between an acquisition layer of an absorbent structure and the associated absorbent core has been found to desirably reduce Rewet. Furthermore, the use of a dryness layer alone, without an acquisition layer, has been found unexpectedly to reduce Plate Wetness and Rewet as well or better than an acquisition layer alone, thus enhancing comfort for the wearer.

In accordance with disclosed embodiments of the invention, an absorbent structure is provided which comprises an absorbent core; and a dryness layer laminate positioned in liquid-transferring relationship with the absorbent core. The dryness layer laminate comprises a carrier substrate, and a matrix of superabsorbent particles and adhesive filaments or fibers, with said superabsorbent particles stabilized on said carrier substrate by said adhesive filaments.

Notably, the dryness layer laminate cooperates with the absorbent core to permit passage of liquid through the dryness layer laminate for retention of the liquid by the absorbent core, with superabsorbent particles in the dryness layer laminate functioning to enhance surface dryness of the absorbent structure. In practice, the superabsorbent particles of dryness layer laminate have a basis weight between about 40 and 130 grams per square meter, wherein the dryness layer laminate exhibits liquid permeability of at least about 40 seconds for Anarewet acquisition time test. Details of the Anarewet acquisition test and a GATS demand absorbency test will be fully discussed in later sections.

In the preferred form, the dryness layer laminate exhibits liquid permeability of at least about 10 grams absorbed after 100 seconds for GATS demand absorbency test, and a coefficient of variation (COV) of the basis weight of the superabsorbent particles layer laminate greater than about 5%. COV is the standard deviation of a basis weight measurement divided by its mean value times 100% for 30 mm diameter circular samples cut from the dryness layer materials. Nine samples were cut from each laminate, three in the machine direction and three in the cross direction, in triplicate, for a total of 27 samples.

To achieve the desired permeability of the dryness layer laminate, the carrier substrate of the laminate comprises tissue having a basis weight of no more than about 20 grams per square meter, and exhibiting a Frazier porosity of at least about 120 ft3/min/ft2. In the preferred embodiment, the carrier substrate of the laminate comprises first and second layers of tissue, with the matrix of superabsorbent particles and adhesive filaments positioned between and joining the two layers of tissue.

The adhesive filaments of the dryness layer laminate preferably comprise no more than about 4 weight percent of the superabsorbent particles of the laminate, more preferably no more than about 3 weight percent of the superabsorbent particles.

In the preferred practice of the invention, the absorbent core of the absorbent structure comprises a blend of cellulosic fibers and particulate superabsorbent.

In another aspect of the invention, an absorbent structure is provided which comprises an absorbent core, an upper acquisition layer and a dryness layer laminate positioned in liquid-transferring relationship between the acquisition layer and the absorbent core. The dryness layer laminate comprises a carrier substrate including first and second tissue layers, and a matrix of superabsorbent particles and adhesive filaments, with the superabsorbent particles stabilized between the first and second tissue layers of the carrier substrate by the adhesive filaments.

The first and second tissue layers of the carrier substrate each having a basis weight of no more than about 20 grams per square meter, and a Frazier porosity of at least about 120 ft3/min/ft2, with the adhesive filaments of the dryness layer laminate comprising no more than about 4 weight percent of the superabsorbent particles. The superabsorbent particles of the dryness layer have a basis weight between about 40 and 130 grams per square meter, wherein a coefficient of variation (COV) of the basis weight of said superabsorbent particles in the dryness layer laminate is greater than about 5%. By this structure, the dryness layer laminate cooperates with said absorbent core to permit passage of liquid through the dryness layer for retention of the liquid by the absorbent core, such that the dryness layer laminate retains an amount of liquid that is less than 60% of its available capacity in the Anarewet acquisition test. Notably, the superabsorbent particles in the dryness layer laminate function to enhance surface dryness of the absorbent structure by removal of liquid from said nonwoven coverstock material. Preferably, the absorbent core comprises a blend of cellulosic fibers and particulate superabsorbent Preferably, the adhesive filaments of the dryness layer laminate comprise no more than about 3 weight percent of the superabsorbent particles of the laminate. To achieve the desired performance, the dryness layer laminate comprises a sufficient quantity of said superabsorbent particles to yield at least 1200 grams per square meter centrifuge retention capacity (CRC) in 0.9% saline solution to enhance removal of liquid from said acquisition layer.

In another aspect of the present invention, an absorbent core system is disclosed which comprises an absorbent core comprised of cellulosic fibers, an upper, synthetic nonwoven acquisition layer, and a dryness layer laminate, disposed between the absorbent core and the synthetic nonwoven acquisition layer. The dryness layer laminate comprises first and second layers of tissue substrate, and a mixture of superabsorbent polymer and hot melt adhesive fibers between said first and second tissue substrates. The superabsorbent polymer particles having a basis weight of between about 40 grams per square meter and 130 grams per square meter. The dryness layer laminate exhibits a basis weight coefficient of variation (COV) in superabsorbent polymer basis weight between 5% and 25%, wherein the only cellulosic fiber disposed between the superabsorbent polymer particles in the dryness layer laminate and the adjacent synthetic nonwoven layers is that cellulosic fiber which comprises the tissue substrate of the dryness layer laminate.

Numerous other features and advantages of the present invention will become readily apparent from the following detailed description, the accompanying drawings, and the appended claims.

DETAILED DESCRIPTION OF THE INVENTION

While the present invention is susceptible of embodiment in various forms, there is shown in the drawings and will hereinafter be described presently preferred embodiments of the invention, with the understanding that the present disclosure is intended to be an exemplification of the invention, and is not intended to be limited to the specific embodiments disclosed herein.

The present invention is directed to an adhesively-bonded laminate of superabsorbent polymer, or dryness layer that can be placed on the surface of an absorbent core to enhance or boost surface dryness without a meaningful increase in liquid acquisition time. Notably, disposition of the dryness layer laminate between an acquisition layer of an absorbent structure and the associated absorbent core has been found to desirably reduce Rewet and Plate Wetness, thus enhancing comfort for the wearer.

As will be further described, an absorbent structure is provided which comprises an absorbent core, and a dryness layer laminate positioned in liquid-transferring relationship with said absorbent core. The dryness layer laminate comprises a carrier substrate comprised of tissue, and a matrix of superabsorbent particles and adhesive filaments or fibers, with said superabsorbent particles stabilized on said carrier substrate by said adhesive filaments.

Notably, the dryness layer laminate cooperates with the absorbent core to permit passage of liquid through the dryness layer laminate for retention of the liquid by the absorbent core, with superabsorbent particles in the dryness layer laminate functioning to enhance surface dryness of the absorbent structure. In practice, the superabsorbent particles of dryness layer laminate have a basis weight between about 40 and 130 grams per square meter, wherein the dryness layer laminate exhibits liquid permeability of at least about 40 seconds for Anarewet acquisition time test.

In the preferred form, the dryness layer laminate exhibits liquid permeability of at least about 10 grams absorbed after 100 seconds for GATS demand absorbency test, and a coefficient of variation (COV) of the basis weight of the superabsorbent particles layer laminate greater than about 5%.

To achieve the desired permeability of the dryness layer laminate, the carrier substrate of the laminate comprises at least one tissue layer having a basis weight of no more than about 20 grams per square meter, and exhibiting a Frazier porosity of at least about 120 ft$^3$/min/f$^2$. In the preferred embodiment, the carrier substrate of the laminate comprises first and layers of said tissue each having this basis weight and porosity, with the matrix of superabsorbent particles and adhesive filaments positioned between and joining said two layers of tissue. The adhesive filaments of the dryness layer laminate preferably comprise no more than about 4 weight percent of the superabsorbent particles of the laminate, more preferably no more than about 3 weight percent of the superabsorbent particles. In the preferred practice of the invention, the absorbent core of the absorbent structure comprises a blend of cellulosic fibers and particulate superabsorbent.

In an illustrated embodiment of the invention, an absorbent structure is provided which comprises an absorbent core, an acquisition layer and a dryness layer laminate positioned in liquid-transferring relationship between the acquisition layer and the absorbent core, the dryness layer laminate comprises a carrier substrate including first and second tissue layers, and a matrix of superabsorbent particles and adhesive filaments, with the superabsorbent particles stabilized between the first and second tissue layers of the carrier substrate by the adhesive filaments. The first and second tissue layers of the carrier substrate preferably each having a basis weight of no more than about 20 grams per square meter, and a Frazier porosity of at least about 120, with the adhesive filaments of the dryness layer laminate comprising no more than about 4 weight percent of the superabsorbent particles.

The superabsorbent particles of the dryness layer have a basis weight between about 40 and 130 grams per square meter, wherein a coefficient of variation (COV) of the basis weight of said superabsorbent particles in the dryness layer laminate is greater than about 5%. By this structure, the dryness layer laminate cooperates with the absorbent core to permit passage of liquid through the dryness layer for retention of the liquid by the absorbent core, such that the dryness layer laminate retains an amount of liquid that is less than 60% of its available capacity in the Anarewet acquisition test. Notably, the superabsorbent particles in the dryness layer laminate function to enhance surface dryness of the absorbent structure by removal of liquid from said adjacent nonwoven layer. Preferably, the absorbent core comprises a blend of cellulosic fibers and particulate superabsorbent Preferably, the adhesive filaments of the dryness layer laminate comprise no more than about 3 weight percent of the superabsorbent particles of the laminate. To achieve the desired performance, the dryness layer laminate comprises a sufficient quantity of said superabsorbent particles to yield at least 1200 grams per square meter centrifuge retention capacity (CRC) in 0.9% saline solution to enhance removal of liquid from the acquisition layer but preferably less than 130 gsm in basis weight.

In illustrated embodiment of the present invention, an absorbent core system is disclosed which comprises an absorbent core comprised of cellulosic fibers, a synthetic nonwoven acquisition layer, and a dryness layer laminate, disposed between the absorbent core and the synthetic nonwoven acquisition layer. The dryness layer laminate comprises first and second layers of tissue substrate, a mixture of superabsorbent polymer and hot melt adhesive fibers between the first and second tissue substrates, and superabsorbent polymer particles having a basis weight of between about 40 grams per square meter and 130 grams per square meter. The dryness layer laminate exhibits a basis weight coefficient of variation (COV) in superabsorbent polymer basis weight between 5% and 25%, wherein the only cellulosic fiber disposed between the superabsorbent polymer particles in the dryness layer laminate and the synthetic nonwoven acquisition layer is that cellulosic fiber which comprises said first and second tissue substrates of said dryness layer laminate.

Figure 1:
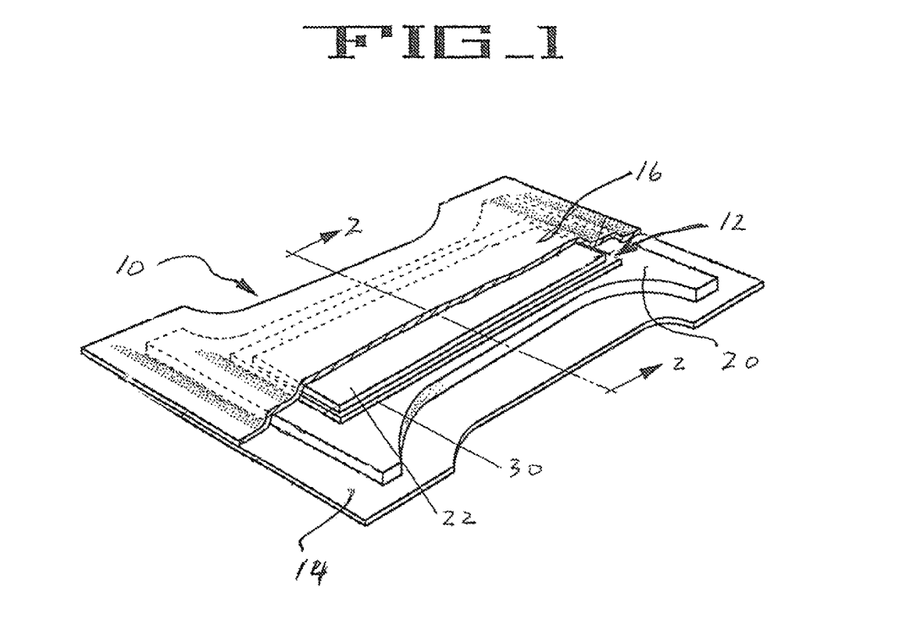
FIG. 1 a diagrammatic, perspective view of a disposable absorbent article configured in accordance with the present invention.
Figure 2:
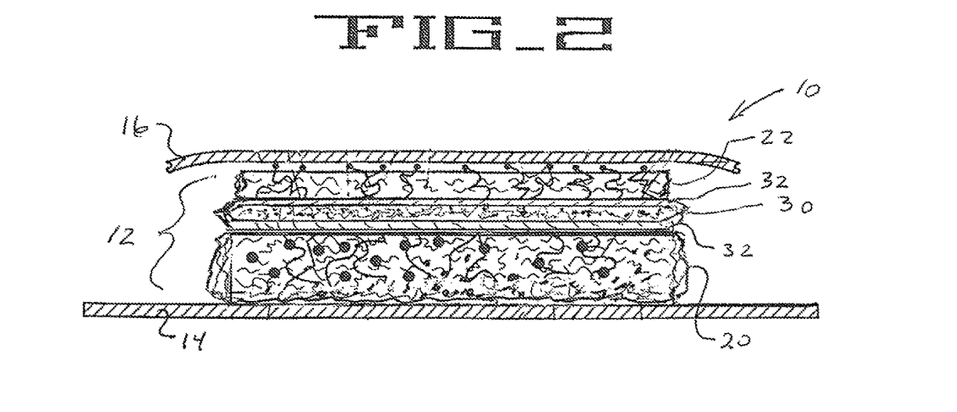
FIG. 2 is a diagrammatic, cross-sectional view of the absorbent article shown in FIG. 1.

With reference now to FIGS. 1 and 2, therein is illustrated in an exemplary absorbent article 10 having an absorbent structure 12 configured in accordance with the present invention. Absorbent article 10 is a diagrammatic illustration of a typical disposable absorbent article or garment for infant or incontinence care. To this end, the absorbent article 10 includes a typically liquid-impervious back sheet 14 positioned beneath the absorbent structure 12, and a liquid-permeable top sheet 16 positioned on top of the absorbent structure.

In the typical construction, as illustrated, the absorbent structure of the article 10 includes a lower, absorbent core 20, typically comprising comminuted wood pulp, i.e., wood pulp fluff, and particulate superabsorbent (SAP) material. In accordance with a typical structure, the absorbent structure 12 further includes an upper acquisition/distribution layer (ADL) 22, positioned beneath top sheet 16. Acquisition layer 22 may comprise a synthetic nonwoven material, or an apertured polymeric film, which acts to receive liquid, and distribute liquid within the absorbent structure or article. Thereafter, liquid is received and absorbed by the absorbent core 20, with the superabsorbent polymer particulate material in the absorbent core acting to absorb and retain the liquid.

In accordance with the present invention, the absorbent structure 12 includes a dryness layer laminate 30 operatively positioned between the optional acquisition layer 22 and the absorbent core 20, in liquid-transferring relationship therewith.

Dryness layer laminate 30 preferably comprises a substrate in the form of first and second tissue layers 32 with a matrix of filamentary or fibrous adhesive, and superabsorbent particles positioned between the tissue layers 32. The filamentary adhesive desirably acts to stabilize the superabsorbent particles in the dryness layer laminate, while simultaneously adhering and integrating the tissue layers 32.

Formation of dryness laminate layer 30 is further described herein after, with the understanding that the dryness layer can be formed in accordance with the teachings of U.S. Patent Publication No. 2011/0162989, to Ducker et al., the disclosure of which is hereby incorporated by reference.

As discussed, the laminate layer 30 desirably functions to permit transfer of liquid through top sheet 16, optional acquisition layer 22, and to the lower absorbent core 20. This specific configuration of the dryness layer laminate 30 in order to provide functioning in this manner, including the desired porosity of the tissue layers 30, is discussed further hereinafter.

Notably, the superabsorbent particulate material in the dryness layer exhibits sufficient liquid permeability to permit initial movement of liquid downwardly through the dryness layer to the absorbent core 20. However, in order to enhance the dryness of the absorbent article 10 as it contacts the wearer, including top sheet 16, the dryness layer effectively acts to dewater the top sheet 16, even subsequent to initial introduction of liquid into the absorbent article. Testing has shown a significant improvement in "Plate Wetness" which is characterized by a relative dryness of those portions of the absorbent article that contact the wearer.

Figure 3:
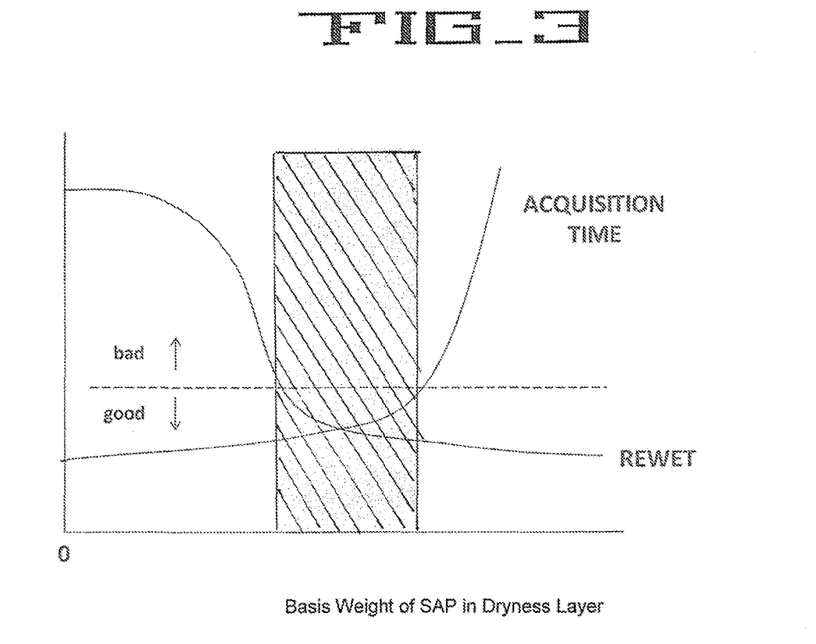
FIG. 3 is a graphical representation showing the optimal basis weight of superabsorbent polymer in a dryness layer laminate to provide simultaneous improvements in surface dryness (Rewet and Plate Wetness) and liquid acquisition (Acquisition time).

With reference now to FIG. 3, therein is a graphical representation showing the optimal basis weight of superabsorbent polymer in the dryness layer laminate 30, in order to provide simultaneous improvements in dryness (i.e. rewet), and liquid acquisition (i.e. acquisition time). As will be appreciated, there is an optimal range for the basis weight of the superabsorbent polymer particles in the dryness layer laminate in order to provide the desired combination of performance characteristics.

EXAMPLES AND TEST METHODS

Two methods were used to characterize the liquid permeability of a dryness layer under realistic conditions of use. The first is a measurement of liquid acquisition time using a Courtray Anarewet device. In this test, a circular sample of dryness layer laminate is placed on a model base core. The base core has sufficient capacity and capillary suction so as to make the permeability of the dryness layer the rate determining factor for acquisition time. The second method is a demand absorbency test on a Gravimetric Absorption Test System (GATS) using the same sample materials.

Results for both tests show that a dryness layer with a low basis weight of SAP had more permeability than one with 0 gsm SAP (i.e. two layers of tissue only). Depending on SAP CRC and mean particle size, there was an optimum in permeability of a dryness layer in the range of 45-89 gsm SAP. Measurement of the CRC of superabsorbent polymers has been described in EDANA Test Method WSP 241.2.R3 (12), hereby incorporated by reference. Lower CRC and higher mean particle size are believed to enhance permeability, at higher SAP basis weights the permeability of the dryness layers decreased to unacceptable levels.

The dryness layers described in TABLES 1 and 2 that follow are comprised of two layers of 17 gsm tissue with Frazier Porosity above 170 ft3/min/ft2, and contain SAP of the basis weight, particle size, and centrifuge retention values described mixed with pressure sensitive synthetic rubber based hot melt adhesive fibers in a quantity less than 3% of the basis weight of the SAP. The COV of the laminate basis weight is above 5% for each. Each sample was tested according to the Anarewet and GATS test procedures described herein. The pooled Coefficient of Variation, or COV, of the Anarewet acquisition time was about 3%. COV is the standard deviation of the test data divided by the mean, expressed as a percentage. The pooled COV of the "GATS Liquid Absorbed after 100 seconds" was about 3%.

The novel structure of the laminate of the present invention promotes passage of liquid through the dryness layer for retention of the liquid by the absorbent core, such that the dryness layer laminate retains an amount of liquid that is much less than its total capacity, typically less than 60% of its capacity, in the Anarewet acquisition test. For example, the total liquid absorption under a pressure of 0.3 psi (see EDANA Test Method "Absorption Under Pressure" WSP 243.2.R1(12)) for the dryness layer used to make Sample #4 in TABLE 1 that contained 89 grams per square meter of superabsorbent polymer, was 18.2 g/g or 20.2 g. of liquid for the 100 mm diameter dryness layer. During the Anarewet acquisition test, approximately 45 g. of saline solution passed through the dryness layer as that liquid was absorbed by the sample. The weight of the dryness layer after the test showed that the dryness layer retained 7.9 g. of liquid, or only 39% of its available capacity under a load of 0.3 psi.

Anarewet Acquisition Time

Anarewet Acquisition time was determined to provide a relevant measure of liquid permeability of a dryness layer laminate. The test was performed using an Anarewet device manufactured by Courtray Consulting, Douai, France. A circular test sample was a single layer of a dryness layer laminate placed on the surface of a model absorbent core that provided sufficient capillary tension and liquid capacity so as to render the dryness layer the rate-controlling layer for liquid absorption in the test sample. Both laminate and model core had a diameter of 100 mm.

The model absorbent core was comprised of four layers of fluff pulp and superabsorbent polymer, each layer hydrogen-bonded between two layers of 17 gsm tissue. The total basis weight of each layer was 140 gsm and the superabsorbent polymer composition was 28%. The superabsorbent polymer in the model core had a centrifuge retention capacity of 46 g/g. The caliper of each layer of the model core was 0.75 mm+/−0.05 mm. The Anarewet device was programmed to apply 20 millibar of pressure to the test samples. Three doses of 15 ml of 0.9% saline solution at a temperature of 22 degrees C. were administered to the samples at an interval of 15 minutes. The time in seconds (+/−1 sec) for each sample to absorb the liquid dose was recorded as the Anarewet Acquisition time.

GATS Liquid Absorbed after 100 Seconds

GATS Liquid Absorbed after 100 seconds provided a relevant measure of liquid permeability of a dryness layer laminate. The test was performed using a Model MK500 Gravimetric Absorbency Test System or GATS manufactured by M/K Systems, Peabody, Mass. A circular test sample was a single layer of a dryness layer laminate placed on the surface of a model absorbent core that provided sufficient capillary tension and liquid capacity so as to render the dryness layer the rate-controlling layer for liquid absorption in the test sample. Both laminate and model core had a diameter of 60 mm.

The model absorbent core was comprised of four layers of fluff pulp and superabsorbent polymer, each layer hydrogen-bonded between two layers of 17 gsm tissue. The total basis weight of each layer was 140 gsm and the superabsorbent polymer composition was 28%. The superabsorbent polymer in the model core had a centrifuge retention capacity of 46 g/g. The caliper of each layer of the model core was 0.75 mm+/−0.05 mm. Demand absorbency of the sample was initiated by placing the sample with the surface dryness layer in direct contact with a fritted glass plate at 0 mm hydrostatic tension. The 75 mm thick VitraPOR fritted glass plate had a porosity of Class 0 (ISO/4793 P250, 160-250 µm). The amount of a 0.9% saline solution at 22 degrees C. absorbed by the test sample after 100 seconds was recorded in grams (+/−0.1 g.) as the GATS Liquid Absorbed after 100 seconds.

Liquid Acquisition, Rewet, and Plate Wetness Test

A conventional Liquid Acquisition and Rewet test to assess absorbent core performance was performed according to the following procedure. Liquid Acquisition was the time in seconds for a 300 mm×100 mm section of an absorbent core to absorb 100 ml of 0.9% saline solution at 22 degrees C. through a 2 in. diameter dosing head. The 300 mm×100 mm section of the core was cut from the center of an absorbent core from an absorbent product and placed on a compliant foam pad.

Absorbent cores were made at a target fluff pulp density of 0.08 g/cc. This was calculated by taking the basis weight of the fluff pulp only (not including any superabsorbent polymer content) in grams per square meter, dividing by the caliper in millimeters, and then dividing by 1000 to yield fluff density in units of grams per cubic centimeter. The cores were covered with a layer of 12 gsm surfactant-treated spunbond polypropylene coverstock. The ends of the cores and coverstock were taped flat to the lab top surface beyond the edges of the foam pad in order to maintain a nominal tension during swelling of the core.

Three to five samples of each prototype core were tested. The dosing head was weighted and had a screen on one end to apply an even pressure of 0.5 psi to the core at the point of liquid dosing. The remainder of the core was restrained under a 150 mm×300 mm cast acrylic plate that weighted 600 g. The dosing head extended through a hole drilled through the center of the plate such that dosing occurred at the center of the core.

A 100 ml. dose of liquid was metered to the dosing head at a rate of 20 ml/sec and the time to absorb the liquid was recorded as the acquisition time (+/−0.1 sec). After 30 minutes of equilibration, the restraining plate was removed, and a stack of ten filter papers (Whatman 4, 70 mm diameter) was placed on the dosing area under a cylindrical brass weight of 60 mm diameter. The weight applied a pressure of 0.84 psi. After precisely two minutes, the weight was removed and Rewet was determined from a difference in weight between the wet and dry filter papers (+/−0.01 g.).

Plate Wetness was determined when the restraining plate was removed from the core. A paper towel was used to collect liquid still attached to the plate after the plate had been removed from the core. A single paper towel was used to remove the liquid from three to five plates used for replicate samples. The mass of liquid from the plates was determined from a difference in weight between the wet and dry paper towel (+/−0.01 g.). An average Plate Wetness for each replicate was determined by dividing the total mass of liquid collected from the plates by the number of replicates. The steps were repeated for four doses of 100 ml of liquid.

TABLE 1

Liquid permeability of dryness layer as a function of CRC, mean particle size, and basis weight of SAP in dryness layer

| Sample | CRC of SAP in Dryness Layer (g/g) | Mean Particle Size of SAP in Dryness Layer (μm) | SAP BW in Dryness Layer (gsm) | Anarewet Acquisition time (sec) Dose 1 | Dose 2 | Dose 3 | Liquid Absorbed after 100 sec. (g) |
|---|---|---|---|---|---|---|---|
| 1. | Base Core and Tissue | — | 0 | 11 | 22 | 47 | 11.8 |
| 2. | 42 | 450 | 45 | 7 | 15 | 28 | 12.4 |
|    |    |     | 60 | 8 | 16 | 30 | 12.8 |
|    |    |     | 89 | 7 | 19 | 34 | 12.5 |
|    |    |     | 125 | 6 | 19 | 167 | 10.0 |
|    |    |     | 168 | 6 | 39 | 422 | 6.9 |
| 3. | 34 | 380 | 45 | 7 | 18 | 25 | 12.0 |
|    |    |     | 60 | 8 | 17 | 36 | 12.9 |
|    |    |     | 89 | 8 | 24 | 55 | 9.4 |
|    |    |     | 125 | — | — | — | 5.9 |
| 4. | 30 | 400 | 45 | — | — | — | — |
|    |    |     | 60 | 8 | 15 | 27 | 11.4 |
|    |    |     | 89 | 7 | 17 | 29 | 12.1 |
|    |    |     | 125 | 8 | 20 | 33 | 8.4 |
|    |    |     | 168 | 7 | 22 | 52 | 6.8 |

The effect of permeability of the dryness layer can be seen in liquid acquisition and Rewet tests of an absorbent core with increasing basis weight of superabsorbent polymer in the dryness layer (TABLE 2). These cores were constructed without an acquisition layer. Acquisition time increased with increasing basis weight of superabsorbent polymer but Rewet and Plate Wetness decreased. Optimal performance in this example was obtained for 54 gsm of superabsorbent polymer in the dryness layer. Pooled COV's of the fourth dose liquid acquisition time, fourth dose Rewet, and fourth dose Plate Wetness were about 4%, 6%, and 5%, respectively. Fourth dose test values typically have the greatest variability.

TABLE 2

Acquisition/Rewet of W112A/W112A absorbent core without ADL as a function of basis weight of T9030 SAP (CRC = 30 g/g) in dryness layer

| Sample | CRC of SAP in Dryness Layer (g/g) | SAP BW in Dryness Layer (gsm) | 100 ml Dose | Acquisition time (sec) | Rewet (g) | Plate Wetness (g) |
|---|---|---|---|---|---|---|
| 1. | — | No tissue | 1 | 32 | 0 | 0 |
|    |   |           | 2 | 35 | 0.1 | 0.08 |
|    |   |           | 3 | 52 | 0.4 | 0.25 |
|    |   |           | 4 | 57 | 6 (sat.) | 0.41 |

TABLE 2-continued

Acquisition/Rewet of W112A/W112A absorbent core without ADL as a function of basis weight of T9030 SAP (CRC = 30 g/g) in dryness layer

| Sample | CRC of SAP in Dryness Layer (g/g) | SAP BW in Dryness Layer (gsm) | 100 ml Dose | Acquisition time (sec) | Rewet (g) | Plate Wetness (g) |
|---|---|---|---|---|---|---|
| 2. | 30 | 54 | 1 | 24 | 0 | 0 |
|  |  |  | 2 | 36 | 0.1 | 0.02 |
|  |  |  | 3 | 64 | 0.4 | 0.05 |
|  |  |  | 4 | 68 | 2.7 | 0.03 |
| 3. | 30 | 60 | 1 | 26 | 0 | 0 |
|  |  |  | 2 | 41 | 0.1 | 0.02 |
|  |  |  | 3 | 69 | 0.6 | 0.05 |
|  |  |  | 4 | 86 | 5.2 | 0.04 |
| 4. | 30 | 89 | 1 | 27 | 0 | 0 |
|  |  |  | 2 | 59 | 0.1 | 0.01 |
|  |  |  | 3 | 107 | 0.2 | 0.02 |
|  |  |  | 4 | 117 | 0.9 | 0.03 |
| 5. | 30 | 168 | 1 | 27 | 0 | 0 |
|  |  |  | 2 | 79 | 0.1 | 0.00 |
|  |  |  | 3 | 179 | 0.2 | 0.00 |
|  |  |  | 4 | 189 | 0.8 | 0.00 |

Performance of Dryness Layers in Absorbent Cores without an ADL

Measurements of the acquisition time and dryness of absorbent cores without an ADL (acquisition/distribution layer) provide fundamental insight into the performance of a core with and without a dryness layer laminate. An acquisition layer can cause liquid to spread over the surface of a slowly-absorbing core and mask real liquid absorption into the core. The third and fourth dose Rewet of Sample 2 with a dryness layer (TABLE 3) was much improved over that of Sample 1 that did not have a dryness layer. Acquisition times for cores with the dryness layer were somewhat higher, but still acceptable for use in most absorbent products. The amount of SAP in the dryness layer was 1.5 g. but Sample 3 shows that it was not possible to achieve the same level of dryness by increasing SAP over the same area in the surge core by 2.8 g. (i.e. from 7.4 to 10.2 g.). The quantity of SAP required to achieve the dryness provided by the dryness layer would be costly, difficult to convert, and it is believed that it would increase acquisition times to an unacceptable level.

The results in TABLES 4 and 5 show similar results obtained with superabsorbent polymers with higher values of CRC in the surge core. Key results are summarized in TABLE 6. These examples show that the dryness layer laminate is robust and can provide improvements in Rewet without acquisition layers on a variety of fluff/SAP absorbent cores containing different superabsorbent polymers. For the absorbent core in TABLE 4, made with a dryness layer containing 54 gsm of T9030 SAP (CRC=30 g/g) according to Material Example 1, 4th dose Acquisition time was increased by 26% from 54 to 68 seconds, 4th dose Rewet was decreased by 55% from 6 g. to 2.7 g., and Plate Wetness after the 4th dose was reduced by 70% from 0.100 g. to 0.030 g. This was an acceptable increase in acquisition time for much improved surface dryness (i.e. Rewet and Plate Wetness). Rewet values of 6 (sat.) g. indicate that the filter paper used to measure the Rewet was completely saturated and that the actual amount of liquid expressed from the core could have been higher. This high value of Rewet indicates a surface that is unacceptably wet to the touch.

TABLE 3

Acquisition/Rewet of 7075/W211 absorbent core without ADL, with and without 54 gsm T9030 dryness layer (material example 1), compared to core with additional 7075 SAP in surge core

| | Sample No. and Description of Absorbent Core | 100 ml Dose | Acquisition time (sec) | Rewet (g) |
|---|---|---|---|---|
| 1. | Size Large Adult Brief Core | 1 | 28 | 0 |
|  | Surge Core: 15.1 g. Fluff/7.4 g. T7075 SAP | 2 | 34 | 0.2 |
|  | Base Core: 40.6 g. Fluff/4.0 g. W211 SAP | 3 | 50 | 1.0 |
|  | Dryness Layer: None | 4 | 73 | 4.6 |
| 2. | Size Large Adult Brief Core | 1 | 30 | 0 |
|  | Surge Core: 15.1 g. Fluff/7.4 g. T7075 SAP | 2 | 39 | 0 |
|  | Base Core: 40.6 g. Fluff/4.0 g. W211 SAP | 3 | 80 | 0.1 |
|  | Dryness Layer: 54 gsm T9030 SAP | 4 | 94 | 0.8 |
| 3. | Size Large Adult Brief Core | 1 | 32 | 0 |
|  | Surge Core: 15.1 g. Fluff/10.2 g. T7075 SAP | 2 | 39 | 0.2 |
|  | Base Core: 40.6 g. Fluff/4.0 g. W211 SAP | 3 | 48 | 0.8 |
|  | Dryness Layer: None | 4 | 74 | 4.5 |

TABLE 4

Acquisition/Rewet of T9030/W211 absorbent core without ADL, with and without 54 gsm T9030 dryness layer according to Material Example 1, compared to core with additional T9030 SAP in surge core

| Sample No. and Description of Absorbent Core | 100 ml Dose | Acquisition time (sec) | Rewet (g) |
|---|---|---|---|
| 1. Size Large Adult Brief Core | 1 | 26 | 0 |
| Surge Core: 15.1 g. Fluff/8.0 g. T9030 SAP | 2 | 38 | 5.9 |
| Base Core: 40.6 g. Fluff/4.0 g. W211 SAP | 3 | 50 | 6 (sat.) |
| Dryness Layer: None | 4 | 57 | 6 (sat.) |
| | | | |
| 2. Size Large Adult Brief Core | 1 | 23 | 0 |
| Surge Core: 15.1 g. Fluff/8.0 g. T9030 SAP | 2 | 30 | 0.3 |
| Base Core: 40.6 g. Fluff/4.0 g. W211 SAP | 3 | 42 | 1.4 |
| Dryness Layer: 54 gsm T9030 SAP | 4 | 54 | 6 (sat.) |
| | | | |
| 3. Size Large Adult Brief Core | 1 | 26 | 0 |
| Surge Core: 15.1 g. Fluff/10.2 g. T9030 SAP | 2 | 38 | 1.3 |
| Base Core: 40.6 g. Fluff/4.0 g. W211 SAP | 3 | 49 | 5.2 |
| Dryness Layer: None | 4 | 52 | 6 (sat.) |

TABLE 5

Acquisition/Rewet of W112A/W112A absorbent core without ADL, with and without 54 gsm T9030 dryness layer

| Sample No. and Description of Absorbent Core | 100 ml Dose | Acquisition time (sec) | Rewet (g) | Plate Wetness (g) |
|---|---|---|---|---|
| 1. Size Medium Adult Brief Core | 1 | 28 | 0 | 0 |
| Surge Core: 13.7 g. Fluff/7.4 g. W112A SAP | 2 | 39 | 0.5 | 0.025 |
| Base Core: 35.8 g. Fluff/3.5 g. W112A SAP | 3 | 52 | 5.0 | 0.095 |
| Dryness Layer: None | 4 | 54 | 6 (sat.) | 0.100 |
| | | | | |
| 2. Size Medium Adult Brief Core | 1 | 24 | 0 | 0 |
| Surge Core: 13.7 g. Fluff/7.4 g. W112A SAP | 2 | 36 | 0.1 | 0.015 |
| Base Core: 35.8 g. Fluff/3.5 g. W112A SAP | 3 | 64 | 0.4 | 0.045 |
| Dryness Layer: 54 gsm T9030 SAP | 4 | 68 | 2.7 | 0.030 |

TABLE 6

Data Summary for absorbent cores with 7075/W211 vs. T9030/W211 absorbent cores, without ADL, both with and without 54 gsm T9030 dryness layer

| Surge Core SAP | ADL | CRC of Surge Core SAP (g/g) | SFC of Surge Core SAP ($10^{-7}$ cm3 sec/g) | 54 gsm T9030 Dryness Layer | $3^{rd}$ Dose Rewet (g) | $4^{th}$ dose Rewet (g) |
|---|---|---|---|---|---|---|
| 7075 | No | 28 | >20 | No | 1.0 | 4.6 |
| 7075 | No | 28 | >20 | Yes | 0.1 | 0.8 |
| T9030 | No | 30 | 5-10 | No | 6 (sat.) | 6 (sat.) |
| T9030 | No | 30 | 5-10 | Yes | 1.4 | 6 (sat.) |
| W112A | No | 34 | 0-5 | No | 5.0 | 6 (sat.) |
| W112A | No | 34 | 0-5 | Yes | 0.4 | 2.7 |

The superabsorbent polymer with a CRC of 28 g/g, the lowest CRC of all polymers tested, unexpectedly provided the best Rewet values with a dryness layer. Furthermore, values of Plate Wetness for Sample #2 in TABLE 3 were below 0.03 g. after all four doses. There was an unexpected favorable interaction for surface dryness between the dryness layer and the absorbent core containing a low CRC (i.e. 28 g/g) superabsorbent polymer in its upper surge core and a high CRC (i.e. 42 g/g) superabsorbent polymer in its lower base core. Saline Flow Conductivity, or SFC, is a measure of the liquid permeability of superabsorbent polymer as described in U.S. Pat. No. 5,669,894 hereby incorporated by reference.

Effect of Tissue Porosity and SAP Variability

TABLE 7 shows that a dryness layer made with nonporous tissue with a porosity around 85 ft3/min/ft2 and a COV of basis weight of superabsorbent polymer of only 3% increased acquisition times to unacceptably high values, although it provided good surface dryness.

TABLE 7

Acquisition/Rewet of W112A/W112A Absorbent Cores without ADL, containing dryness layer constructed with standard tissue and low variability (Coefficient of variation or COV) of SAP basis weight

| Sample No. and Construction of Dryness Layer | 100 ml Dose | Acquisition time (sec) | Rewet (g) | Plate Wetness (g) |
|---|---|---|---|---|
| 1. 54 gsm T9030 SAP with porous tissue and 10% COV of SAP basis weight in dryness layer according to material example 1 | 1 | 24 | 0 | 0 |
| | 2 | 36 | 0.1 | 0.02 |
| | 3 | 64 | 0.4 | 0.05 |
| | 4 | 68 | 2.7 | 0.03 |
| 2. 72 gsm T9030 SAP with standard tissue and 3% COV of SAP basis weight in dryness layer | 1 | 30 | 0 | 0 |
| | 2 | 62 | 0.1 | 0.003 |
| | 3 | 136 | 0.1 | 0.01 |
| | 4 | 154 | 0.4 | 0.01 |
| 3. 89 gsm T9030 SAP with porous tissue and 10% COV of SAP basis weight in dryness layer | 1 | 27 | 0 | 0 |
| | 2 | 59 | 0.1 | 0.01 |
| | 3 | 107 | 0.2 | 0.02 |
| | 4 | 117 | 0.9 | 0.03 |

Performance of Dryness Layers in Absorbent Cores with an ADL

An apertured film acquisition/distribution layer (ADL) (such as available from Tredegar) has been shown to improve the Acquisition time and Rewet of these cores. TABLES 8 & 9 show that the dryness layer provided a meaningful reduction of fourth-dose Rewet to cores made with different types of superabsorbent polymers. T9030 SAP in TABLE 8 had a CRC of 30 g/g and W112A SAP in TABLE 9 had a CRC of 34 g/g. Key results for absorbent cores made with these superabsorbent polymers and constructed with and without a dryness layer, and with and without an acquisition layer, are summarized in TABLE 10.

TABLE 8

Acquisition/Rewet of T9030/W211 absorbent core with ADL, with and without 54 gsm T9030 dryness layer

| Sample No. and Description of Absorbent Core | 100 ml Dose | Acquisition time (sec) | Rewet (g) | Plate Wetness (g) |
|---|---|---|---|---|
| 1. Size Large Adult Brief Core | 1 | 14 | 0 | 0 |
| Surge Core: 15.1 g. Fluff/8.0 g. T9030 SAP | 2 | 14 | 0.4 | 0.14 |
| Base Core: 40.6 g. Fluff/4.0 g. W211 SAP | 3 | 17 | 1.2 | 0.14 |
| Dryness Layer: None | 4 | 19 | 6 (sat.) | 0.20 |
| 2. Size Large Adult Brief Core | 1 | 13 | 0 | 0 |
| Surge Core: 15.1 g. Fluff/8.0 g. T9030 SAP | 2 | 14 | 0.3 | 0.11 |
| Base Core: 40.6 g. Fluff/4.0 g. W211A SAP | 3 | 18 | 0.4 | 0.06 |
| Dryness Layer: 54 gsm T9030 SAP | 4 | 19 | 2.4 | 0.17 |

TABLE 9

Acquisition/Rewet of W112A/W112A absorbent core with ADL, with and without 54 gsm T9030 dryness layer

| Sample No. and Description of Absorbent Core | 100 ml Dose | Acquisition time (sec) | Rewet (g) | Plate Wetness (g) |
|---|---|---|---|---|
| 1. Size Medium Adult Brief Core | 1 | 15 | 0 | 0 |
| Surge Core: 13.7 g. Fluff/7.4 g. W112A SAP | 2 | 17 | 0.1 | 0.02 |
| Base Core: 35.8 g. Fluff/3.5 g. W112A SAP | 3 | 19 | 0.2 | 0.08 |
| Dryness Layer: None | 4 | 22 | 4.7 | 0.10 |
| 2. Size Medium Adult Brief Core | 1 | 15 | 0 | 0 |
| Surge Core: 13.7 g. Fluff/7.4 g. W112A SAP | 2 | 19 | 0.1 | 0.01 |
| Base Core: 35.8 g. Fluff/3.5 g. W112A SAP | 3 | 23 | 0.2 | 0.07 |
| Dryness Layer: 54 gsm T9030 SAP according to material example 1 | 4 | 25 | 0.6 | 0.14 |

Rewet and Plate Wetness were much reduced for cores constructed with a dryness layer comprised of 54 gsm T9030 SAP of the present invention. Rewet for cores constructed with an ADL only was comparable to those constructed with only dryness layer, however, when the cores were constructed with both dryness layer and ADL the effects were additive, and Rewet was lower than could otherwise be obtained using either one alone. Plate Wetness for cores constructed with ADL was not improved significantly by the dryness layer.

TABLE 10

Data Summary for T9030/W211 and W112A/W112A absorbent cores with and without apertured film ADL, and with and without 54 gsm T9030 dryness layer made according to Material Example 1

| Core | 54 gsm, 30 g/g CRC SAP Dryness Layer | Apertured Film ADL | $3^{rd}$ Dose Rewet (g) | $4^{th}$ Dose Rewet (g) | $3^{rd}$ Dose Plate Wetness (g) | $4^{th}$ Dose Plate Wetness (g) |
|---|---|---|---|---|---|---|
| T9030/W211 | No | No | 6 (sat.) | 6 (sat.) | X | X |
| T9030/W211 | Yes | No | 1.4 | 6 (sat.) | X | X |
| T9030/W211 | No | Yes | 1.2 | 6 (sat.) | 0.14 | 0.20 |
| T9030/W211 | Yes | Yes | 0.4 | 2.4 | 0.06 | 0.17 |
| W112A/W112A | No | No | 5.0 | 6 (sat.) | 0.10 | 0.10 |
| W112A/W112A | Yes | No | 0.4 | 2.7 | 0.04 | 0.03 |
| W112A/W112A | No | Yes | 0.2 | 4.7 | 0.08 | 0.10 |
| W112A/W112A | Yes | Yes | 0.2 | 0.6 | 0.07 | 0.14 |

A carded, through-air-bonded (TAB) acquisition layer used with a dryness layer provided comparable Acquisition/Rewet performance to that obtained with the apertured film acquisition layer.

TABLE 10

Acquisition/Rewet of W211A/W211A absorbent core with apertured film and carded, TAB ADL

| | Sample No. and Position of Dryness Layer | 100 ml Dose | Acquisition time (sec) | Rewet (g) | Plate Wetness (g) |
|---|---|---|---|---|---|
| 1. | Film ADL (inverted) with 54 gsm T9030 dryness layer made according to Material Example 1 | 1 | 15 | 0 | 0 |
| | | 2 | 19 | 0.1 | 0.01 |
| | | 3 | 23 | 0.2 | 0.07 |
| | | 4 | 25 | 0.6 | 0.14 |
| 2. | Carded, TAB ADL only, No dryness layer | 1 | 14 | 0 | 0 |
| | | 2 | 13 | 0.4 | 0.10 |
| | | 3 | 16 | 0.4 | 0.12 |
| | | 4 | 19 | 0.4 | 0.16 |
| 3. | Carded, TAB ADL with 54 gsm T9030 dryness layer made according to Material Example 1 | 1 | 14 | 0 | 0 |
| | | 2 | 14 | 0.6 | 0.15 |
| | | 3 | 16 | 0.5 | 0.15 |
| | | 4 | 19 | 0.4 | 0.16 |

Effect of SAP Basis Weight and CRC on Performance of Dryness Layers in Absorbent Cores with an ADL TABLE 11 contains additional performance data for absorbent cores constructed with dryness layers containing different basis weights of the T9030 superabsorbent polymer. The acquisition layer masked the liquid absorption characteristics of the absorbent core and dryness layer, however the results showed a modest increase in acquisition time with increasing basis weight of superabsorbent polymer in the dryness layer. Fourth dose Rewet was much improved for cores constructed with a dryness layer. The dryness layer did not improve the Plate Wetness of absorbent cores constructed with an acquisition layer.

TABLE 11

Acquisition/Rewet of W112A/W112A absorbent core with ADL as a function of basis weight of T9030 SAP (CRC = 30 g/g) in dryness layer

| Sample | CRC of SAP in Dryness Layer (g/g) | SAP BW in Dryness Layer (gsm) | 100 ml Dose | Acquisition time (sec) | Rewet (g) | Plate Wetness (g) |
|---|---|---|---|---|---|---|
| 1. | No Dryness Layer | No Dryness Layer | 1 | 15 | 0 | 0 |
| | | | 2 | 17 | 0.1 | 0.02 |

TABLE 11-continued

Acquisition/Rewet of W112A/W112A absorbent core with ADL as a function of basis weight of T9030 SAP (CRC = 30 g/g) in dryness layer

| Sample | CRC of SAP in Dryness Layer (g/g) | SAP BW in Dryness Layer (gsm) | 100 ml Dose | Acquisition time (sec) | Rewet (g) | Plate Wetness (g) |
|---|---|---|---|---|---|---|
|  |  |  | 3 | 19 | 0.2 | 0.08 |
|  |  |  | 4 | 22 | 4.7 | 0.10 |
| 2. | 30 | 54 | 1 | 15 | 0 | 0 |
|  |  |  | 2 | 19 | 0.1 | 0.01 |
|  |  |  | 3 | 23 | 0.2 | 0.07 |
|  |  |  | 4 | 25 | 0.6 | 0.14 |
| 3. | 30 | 60 | 1 | 16 | 0 | 0 |
|  |  |  | 2 | 19 | 0.1 | 0.00 |
|  |  |  | 3 | 23 | 0.1 | 0.04 |
|  |  |  | 4 | 26 | 0.3 | 0.12 |
| 4. | 30 | 89 | 1 | 16 | 0 | 0 |
|  |  |  | 2 | 22 | 0.1 | 0.02 |
|  |  |  | 3 | 27 | 0.1 | 0.02 |
|  |  |  | 4 | 29 | 0.3 | 0.12 |
| 5. | 30 | 168 | 1 | 16 | 0 | 0 |
|  |  |  | 2 | 23 | 0.1 | 0.01 |
|  |  |  | 3 | 28 | 0.1 | 0.02 |
|  |  |  | 4 | 32 | 0.2 | 0.11 |

General Process:

To produce the dryness layer laminate of the present invention, hot melt adhesive is used to laminate a substantially continuous layer of SAP particles between two layers of tissue substrates to form a sandwich structure.

In a preferred embodiment the laminate of the present invention is made by forming the adhesive into microfibers or filaments using one of the meltblown processes commercially available from hot melt equipment manufacturers such as Nordson or ITW Dynatec to produce a random curtain of hot melt adhesive microfibers, and then mixing those fibers with SAP particles which have been metered by any one of the volumetric or gravimetric metering equipment commercially available by equipment suppliers such as K-Tron or Acrison. Forming the SAP into a flattened falling stream and mixing it with the flat curtain of adhesive fibers produced by the hot melt equipment produces a uniform basis weight. This mixture is deposited onto a moving tissue substrate and then another tissue substrate is placed on top of the tacky mixture which the adhesive fibers are still tacky to form a sandwich.

The preferred hot melt adhesive is desirably a pressure-sensitive hot melt adhesive of a type designed and suitable for use in construction of absorbent hygiene articles made in typical high-speed converting processes.

In a preferred embodiment, the hot melt application equipment provides a sufficient degree of fiber attenuation and available glue fiber surface in order to capture the SAP particles so that few are unattached. It has been found that typical commercial application equipment is easily capable of this when set up by those skilled in the art.

In a preferred embodiment, the COV of the basis weight for the SAP in the laminate, as measured by cutting 30 mm circular samples from the laminate and weighing them, is greater than 5%. This will likely be met by depositing the SAP/adhesive fibers onto the substrate as soon as the streams fully penetrated one another but is easily increased by increasing the path of travel of the mixed adhesive/SAP steam before it is deposited onto a substrate.

It is necessary to produce the desired intake rates that the tissue used for the substrate for the dryess layer is a light-weight porous grade. A tissue with Frazier Porosity of 85 ft^3/min/ft^2 is unsuitable. A Frazier porosity of >120 is preferred and >150 is even more preferred. Basis weight is preferably light, less than 20 gsm, and more preferably, around 17 gsm. A suitable 10.5 lb tissue grade is commercially available as 3995 from Clearwater Paper The SAP can be any type designed for use in disposable absorbent articles well known to those skilled in the art used as supplied by the manufacturers. These commercially available SAP types are generally designed to work well in wood pulp fluff/SAP cores and have particle size distributions that are designed to provide good core permeability (favoring larger particles), but also not easily felt or seen in a diaper product (favoring smaller particles). These commercially available particle size distributions are suitable for use in the dryness layer of the present invention for the same reason they are suitable for use in fluff/SAP cores.

Adhesive content is ideally kept to a minimal level. Adhesive add-on should not exceed 3.5% of the basis weight of the SAP, and more ideally would be kept below 3% of the SAP and even more ideally would be kept below 2% of the SAP basis weight.

Material Example 1

Material Example 1 was made as a continuous web by unwinding a 10.5#3995 tissue substrate with a basis weight of around 17 gsm from Clearwater Paper and feeding it at about 100 meters per minute. NW 1023 AAZP hot melt adhesive from HB Fuller was melted and processed through an ITW Dynatec hot melt glue system with a UFD head fitted with Omega 5,5 nozzles and sprayed at a roughly 45-degree angle onto the moving tissue web from a distance of about 3-inches. A continuous stream of T9030 SAP from BASF was continuously metered using volumetric means and was formed into a flattened stream about 1 mm thick directed at a 45-degree angle to intersect with the hot melt adhesive stream at about 20 mm above the web, causing the SAP to mix with the adhesive fibers and be deposited together onto the moving tissue. The SAP was fed at an add-on of 27 gsm and the adhesive was fed at an add-on of 0.5 gsm.

A second similar layer of SAP and adhesive, again at 27 gsm and 0.5 gsm add-on respectively was deposited in a similar manner on top of the first.

A second layer of 3995 tissue was fed at a rate matching the speed of the continuous web and was laminated to the SAP and Adhesive mixture on the first web to form a sandwich structure.

Description of Absorbent Core

The absorbent cores in TABLES 3-11 had upper and lower layers comprised of fluff and superabsorbent polymer. The lower layer was a saddle-shaped core, whereas the upper, or surge layer, was a partial length rectangular core with a nonwoven core wrap. Acquisition layer, if present, was the length of the upper surge core. Different superabsorbent polymers can be used in the upper and lower cores.

TABLE 12

Specifications of absorbent cores used to evaluate dryness layer laminates

| | Upper Surge Core | | | | | | Lower Base Core | | | | | |
|---|---|---|---|---|---|---|---|---|---|---|---|---|
| | Fluff | | SAP | | | | Fluff | | SAP | | | |
| | BW (gsm) | Wt. (g) | BW (gsm) | Wt. (g) | SAP % | SAP Type | BW (gsm) | Wt. (g) | BW (gsm) | Wt. (g) | SAP % | SAP Type |
| Absorbent Cores in TABLES 3, 4, 5, & 8 | 457 | 15 | 245 | 8 | 35% | X | 350 | 41 | 35 | 4 | 9% | X or Y |
| | | | Rectangular | | | | | | Shaped | | | |
| | | | Length = 330 mm; Width = 100 mm | | | | | | Length = 680 mm; Middle/End Width = 120 mm/229 mm | | | |
| Absorbent Cores in TABLES 2, 7, 9, 10, & 11 | 457 | 14 | 245 | 7 | 35% | X | 350 | 36 | 35 | 3 | 9% | X or Y |
| | | | Rectangular | | | | | | Shaped | | | |
| | | | Length = 300 mm; Width = 100 mm | | | | | | Length = 600 mm; Middle/End Width = 120 mm/229 mm | | | |

From the above, it will be appreciated that a particularly effective absorbent core system is provided, which is devoid of an acquisition layer positioned above the dryness layer. The system includes an absorbent core comprising upper and lower layers, each comprising a blend of wood pulp fibers and superabsorbent polymer. The absorbent core system further includes a dryness layer in accordance with the present invention position above the absorbent core in liquid-transferring relationship therewith, with the dryness layer thus positioned between the absorbent core and the wearer.

Very desirable performance is achieved where the superabsorbent polymer in the upper layer comprising about 35 weight percent of said blend of wood pulp fibers and superabsorbent polymer in that layer, with the superabsorbent polymer exhibiting a centrifuge retention capacity of about 30 grams/gram. The superabsorbent polymer in the lower layer of the absorbent core comprises about 9 weight percent of the blend of wood pulp fibers and superabsorbent polymer in the lower layer, with the superabsorbent polymer in this layer exhibiting a centrifuge retention capacity of at least about 40 grams/gram.

In this embodiment, in accordance with the present invention, the dryness layer comprises a substrate, filamentary adhesive, and superabsorbent polymer stabilized on the substrate by the filamentary adhesive. The superabsorbent polymer in the dryness layer has a basis weight about 54 grams per square meter, and exhibits a centrifuge retention capacity of less than about 30 grams/gram.

Notably, this embodiment of the present invention exhibits a Fourth Dose Rewet value less than about 1 gram, and a Fourth Dose Plate Wetness of less than about 0.1 grams. As such, this absorbent core system, without the associated acquisition layer, provides Rewet performance comparable to that of an absorbent core provided with a conventional acquisition/distribution layer, as well as improved (lower) Plate Wetness than an absorbent core with a conventional acquisition/distribution layer.

From the foregoing, it will be observed that numerous modifications and variations can be effected without departing from the true spirit and scope of the novel concept of the present invention. It is to be understood that no limitation with respect to the specific embodiments disclosed herein is intended or should be inferred. The disclosure is intended to cover, by the appended claims, all such modifications as fall within the scope of the claims.

What is claimed is:

1. An absorbent structure, comprising:
an absorbent core; and
a dryness layer laminate positioned in liquid-transferring relationship with the absorbent core, the dryness layer laminate comprising a carrier substrate, and a matrix of superabsorbent particles and adhesive filaments, wherein the superabsorbent particles are stabilized on the carrier substrate by the adhesive filaments, wherein the dryness layer laminate is configured with a coefficient of variation (COV) of the basis weight of the superabsorbent particles throughout the dryness layer laminate being between about 5% and about 25% so that the dryness layer laminate cooperates with the absorbent core to permit passage of liquid through the dryness layer laminate for retention of the liquid by the absorbent core, wherein the superabsorbent particles in the dryness layer laminate are configured to enhance surface dryness of the absorbent structure, and wherein the superabsorbent particles in the dryness layer laminate have a basis weight between about 40 and about 130 grams per square meter.

2. The absorbent structure of claim 1, wherein the dryness layer laminate exhibits liquid permeability of at least 40 seconds for the Anarewet acquisition time test.

3. The absorbent structure of claim 1, wherein the carrier substrate of the dryness layer laminate comprises tissue having a basis weight of no more than 20 grams per square meter, and a Frazier porosity of at least 120 ft3/min/ft2.

4. The absorbent structure of claim 3, wherein the carrier substrate comprises first and second layers of the tissue, wherein the matrix of superabsorbent particles and adhesive filaments is positioned between and adjoins the first and second layers of tissue.

5. The absorbent structure of claim 1, wherein the adhesive filaments of the dryness layer laminate comprise no more than 4 weight percent of the superabsorbent particles of the dryness layer laminate.

6. The absorbent structure of claim 5, wherein the adhesive filaments of the dryness layer laminate comprise no more than 3 weight percent of the superabsorbent particles of the dryness layer laminate.

7. The absorbent structure of claim 1, wherein the absorbent core comprises a blend of cellulosic fibers and particulate superabsorbent.

8. An absorbent structure comprising:
an absorbent core;
an acquisition layer; and
a dryness layer laminate positioned in liquid-transferring relationship between the acquisition layer and the absorbent core, wherein the dryness layer laminate comprises:
  a) a carrier substrate having first and second tissue layers, and
  b) a matrix of superabsorbent particles and adhesive filaments,
  wherein the superabsorbent particles are stabilized between the first and second tissue layers of the carrier substrate by the adhesive filaments, wherein the first and second tissue layers of the carrier substrate each have a basis weight of no more than 20 grams per square meter, wherein the adhesive filaments of the dryness layer laminate comprising no more than 4 weight percent of the superabsorbent particles of the dryness layer laminate, wherein the superabsorbent particles of the dryness layer laminate have a basis weight between about 40 and about 130 grams per square meter, wherein a coefficient of variation (COV) of the basis weight of the superabsorbent particles throughout the dryness layer laminate is between about 5% and about 25%, so that the dryness layer laminate cooperates with the absorbent core to permit passage of liquid through the dryness layer laminate for retention of the liquid by the absorbent core, and
wherein the superabsorbent particles in the dryness layer laminate are configured to enhance surface dryness of the absorbent structure.

9. The absorbent structure of claim 8, wherein the adhesive filaments of the dryness layer laminate comprise no more than 3 weight percent of the superabsorbent particles.

10. The absorbent structure of claim 8, wherein the absorbent core comprises a blend of cellulosic fibers and particulate superabsorbent.

11. The absorbent structure of claim 8, wherein the dryness layer laminate comprises a sufficient quantity of the superabsorbent particles to yield at least 1200 grams per square meter centrifuge retention capacity (CRC) in 0.9% saline solution to enhance removal of liquid from the acquisition layer.

12. An absorbent core system, comprising:
a. an absorbent core; and
b. a dryness layer laminate that is comprised of:
  i. first and second layers of tissue substrate, each of the first and second layers of tissue substrate comprised of cellulosic fibers,
  ii. a matrix comprising superabsorbent polymer particles and hot melt adhesive fibers stabilized between the first and second layers of tissue substrate,
  wherein the superabsorbent polymer particles of the dryness layer laminate have a basis weight of between about 40 grams per square meter and about 130 grams per square meter, and wherein a coefficient of variation (COV) of the basis weight of the superabsorbent particles throughout the dryness layer laminate is between about 10% and about 25% so that the dryness layer laminate cooperates with the absorbent core to permit passage of liquid through the dryness layer laminate for retention of the liquid in the absorbent core.

13. An absorbent core system, comprising:
an absorbent core comprising upper and lower layers, each of the upper and lower layers of the absorbent core comprising a blend of wood pulp fibers and superabsorbent polymer, wherein the superabsorbent polymer in the upper layer of the absorbent core comprises about 35 weight percent of the blend of wood pulp fibers and superabsorbent polymer in the upper layer, and exhibits a centrifuge retention capacity of less than 30 grams/gram, wherein the superabsorbent polymer in the lower layer of the absorbent core comprises about 9 weight percent of the blend of wood pulp fibers and superabsorbent polymer in the lower layer, and exhibits a centrifuge retention capacity of at least 40 grams/gram; and
a dryness layer laminate overlying the absorbent core, the dryness layer laminate comprising a substrate, filamentary adhesive, and superabsorbent polymer particles stabilized on the substrate by the filamentary adhesive, wherein the superabsorbent polymer particles of the dryness layer laminate has a basis weight between about 40 and about 130 grams per square meter, wherein a coefficient of variation (COV) of the basis weight of the superabsorbent particles throughout the dryness layer laminate being between about 5% and about 25% so that the dryness layer laminate cooperates with the absorbent core to permit passage of liquid through the dryness layer laminate for retention of the liquid by the absorbent core, and
wherein the absorbent core system is devoid of an acquisition layer positioned above the dryness layer laminate.

14. The absorbent structure of claim 13, wherein the superabsorbent polymer of the dryness layer laminate has a basis weight of about 54 grams per square meter, and exhibits a centrifuge retention capacity of about 30 grams/gram.

15. The absorbent structure of claim 13, wherein the absorbent core system exhibits a Fourth Dose Rewet value less than 1 gram and a Fourth Dose Plate Wetness of less than 0.1 grams.

16. The absorbent structure of claim 1, wherein the dryness layer laminate exhibits liquid permeability of at least 10 grams absorbed after 100 seconds for GATS demand absorbency test.

17. The absorbent structure of claim 1, wherein the matrix of the dryness layer laminate is configured with a coefficient of variation (COV) of the basis weight of the superabsorbent particles that is between about 5% and about 10%.

18. The absorbent structure of claim 8, wherein the first and second tissue layers of the carrier substrate each have a Frazier porosity of at least 120 ft3/min/ft2.

19. The absorbent structure of claim 8, wherein the dryness layer laminate retains an amount of liquid that is less than 60% of the dryness layer laminate's Absorption Under Pressure capacity at 0.3 psi in the Anarewet acquisition test.

20. The absorbent structure of claim 12, further comprising at least one synthetic nonwoven layer overlying the dryness layer laminate; wherein the only cellulosic fibers disposed between the superabsorbent polymer particles in the matrix of the dryness layer laminate and the synthetic nonwoven layer are those cellulosic fibers that comprise one of the first and second tissue substrates.

\* \* \* \* \*

UNITED STATES PATENT AND TRADEMARK OFFICE
CERTIFICATE OF CORRECTION

Page 1 of 1

PATENT NO. : 10,092,674 B2
APPLICATION NO. : 14/212969
DATED : October 9, 2018
INVENTOR(S) : Harry J. Chmielewski and Paul Ducker It is certified that error appears in the above-identified patent and that said Letters Patent is hereby corrected as shown below:

On the Title Page

Add the following considered references to Item (56) References Cited:
U.S. PATENT DOCUMENTS:
2003/0135178 A1        07/2003        Hansen
5,785,696              07/1998        Inoue et al.

FOREIGN PATENT DOCUMENTS:
CN     102970953           03/2013
CN     1230396             10/1999
JP     2003-026701         01/2003
JP     2005-537852         12/2005

OTHER PUBLICATIONS:
Office Action issued in Chinese Patent Application No. 201480021203.7, dated March 02, 2018.
Office Action issued in Japanese Patent Application No. 2016-502781, dated March 26, 2018.

Signed and Sealed this
Second Day of April, 2019

Andrei Iancu
*Director of the United States Patent and Trademark Office*